(12) United States Patent
Neev

(10) Patent No.: US 6,408,212 B1
(45) Date of Patent: Jun. 18, 2002

(54) METHOD FOR TREATING ACNE

(76) Inventor: Joseph Neev, 20321 Lake Forest Dr., Suite D-7, Laguna Beach, CA (US) 92630

( * ) Notice: Subject to any disclaimer, the term of this patent is extended or adjusted under 35 U.S.C. 154(b) by 0 days.

(21) Appl. No.: 09/549,217

(22) Filed: Apr. 13, 2000

Related U.S. Application Data

(60) Provisional application No. 60/129,136, filed on Apr. 13, 1999.
(51) Int. Cl.[7] ................................ A61B 18/18
(52) U.S. Cl. .................. 607/100; 607/109; 128/898; 606/33
(58) Field of Search ................ 128/897–898; 607/1–3, 88–89, 100, 108–109; 606/2, 9, 13, 27, 33; 604/289–291

(56) References Cited

U.S. PATENT DOCUMENTS 5,817,089 A * 10/1998 Tankovich et al. ............. 606/9
6,059,777 A * 5/2000 Acquire ....................... 606/13
6,235,016 B1 * 5/2001 Stewart ......................... 606/9

* cited by examiner

Primary Examiner—Kennedy Schaetzle
Assistant Examiner—Kristen Droesch
(74) Attorney, Agent, or Firm—Price and Gess

(57) ABSTRACT

A method for treatment and modification of material including biological material using an electromagnetic energy source directed to apply the energy to a region of the material, so as to modify and treat a portion of the material in the region. Preferably, an interaction-modifying substance is in the treated region prior to the interaction.

2 Claims, 3 Drawing Sheets

METHOD FOR TREATING ACNE

CROSS-REFERENCE TO RELATED APPLICATION

This application claims priority from U.S. provisional patent application No. 60/129,136, entitled, "A Method for Treating and Preventing Acne and Method for Preserving Skin Elasticity" filed Apr. 13, 1999, which is assigned to the assignee of the present patent application and incorporated herein by reference.

FIELD OF THE INVENTION

The present invention relates generally to the application of energy to biological tissue, and specifically to the application of electromagnetic energy to the skin.

BACKGROUND OF THE INVENTION

It is known in the art to apply electromagnetic energy to biological tissue to engender changes therein. Sunbathers, for example, regularly expose themselves to bright sunlight in order to increase melanocyte activity in the basal layer of the epidermis, responsive to the sun's ultraviolet (UV) radiation. Artificial UV sources have been created to satisfy the desire for a "healthy"-looking tan in the winter. Other forms of electromagnetic energy, laser-light in particular, are currently used in a large range of therapeutic and cosmetic procedures, including eye surgery, hair removal, wrinkle removal, and tattoo removal.

PCT publication WO 98/55035, which is incorporated herein by reference, describes methods for minimizing injury to biological tissue surrounding a site exposed to pulses of electromagnetic energy.

U.S. Pat. No. 5,720,894 to Neev et al., which is incorporated herein by reference, describes biological tissue processing using Ultrashort Pulse High Repetition Rate Laser System for Biological Tissue Processing.

OBJECTS AND SUMMARY OF THE INVENTION

It is an object of some aspects of the present invention to provide improved apparatus and methods for applying energy to a material.

It is another object of some aspects of the present invention to provide improved apparatus and methods for removing heat generated during application of electromagnetic energy to a material.

It is a further object of some aspects of the present invention to provide improved apparatus and methods for removing heat generated during application of electromagnetic energy to biological tissue.

It is still a further object of some aspects of the present invention to provide improved apparatus and methods for decreasing pain during application of electromagnetic energy to biological tissue.

It is yet a further object of some aspects of the present invention to provide improved apparatus and methods for performing medical treatments.

It is also an object of some aspects of the present invention to provide improved apparatus and methods for performing cosmetic treatments.

It is further an object of some aspects of the present invention to provide improved apparatus and methods for enabling a visible wavelength electromagnetic energy source to perform material and tissue removal and modification.

It is yet a further object of some aspects of the present invention to provide methods and apparatus for enabling a visible wavelength electromagnetic energy source to perform material and tissue and modification.

It is also an object of some aspects of the present invention to provide improved methods and apparatus for enabling a low-power electromagnetic energy source to perform tissue removal and modification, substantially without pain, while controlling the amount of damage or modification to remaining tissue.

It is also an object of some aspects of the present invention to provide improved methods and apparatus for enabling a low-power electromagnetic energy source to remove unwanted hair, substantially without pain, while controlling the amount of damage to remaining tissue.

It is also an object of some aspects of the present invention to provide improved methods and apparatus for enabling a low-power electromagnetic energy source to perform tissue treatment that prevent the occurrence of acne.

It is also an object of some aspects of the present invention to provide improved methods and apparatus for enabling a low-power electromagnetic energy source to perform tissue treatment that cures acne and relieves symptoms of acne.

In preferred embodiments of the present invention, the tissue of the subject has been treated with high absorbance substance so that substantially only the hair follicle openings retain the absorbing particles. An energy source applies electromagnetic energy to skin tissue of a subject preferably so as to cause an expansion and clearing of the follicle duct opening. The expanding opening thus allows clearing removal of debris and undesired substances within the hair follicles. Tissue mechanical compression is also preferably applied simultaneous or immediately following the heating and follicular ducts opening action in order to enhance removal of unwanted substance from the hair follicles. Excess heat may be removed by applying a coolant or a cooling element to the tissue. Removal of the heat immediately following the application of the energy generally reduces the subject's sensation of the heat, and, in particular, reduces any sensation of pain. Moreover, heat removal typically reduces or eliminates collateral injury to tissue surrounding the ablated area. Typically, although not necessarily, the tissue comprises the subject's skin.

The tissue of the subject may also be treated by applying a reflective coating material to the skin area being treated and then removing portions of the reflective coating material proximate a blocked hair follicle, for example, and then applying electromagnetic energy to the skin area being treated. The electromagnetic energy is substantially reflected by the reflective coating so as to protect tissue. Where the reflective coating has been removed, the electromagnetic radiation propagates through the tissue so as to mitigate the blockage of a hair follicle.

DETAILED DESCRIPTION OF PREFERRED EMBODIMENTS

Figure 1A:
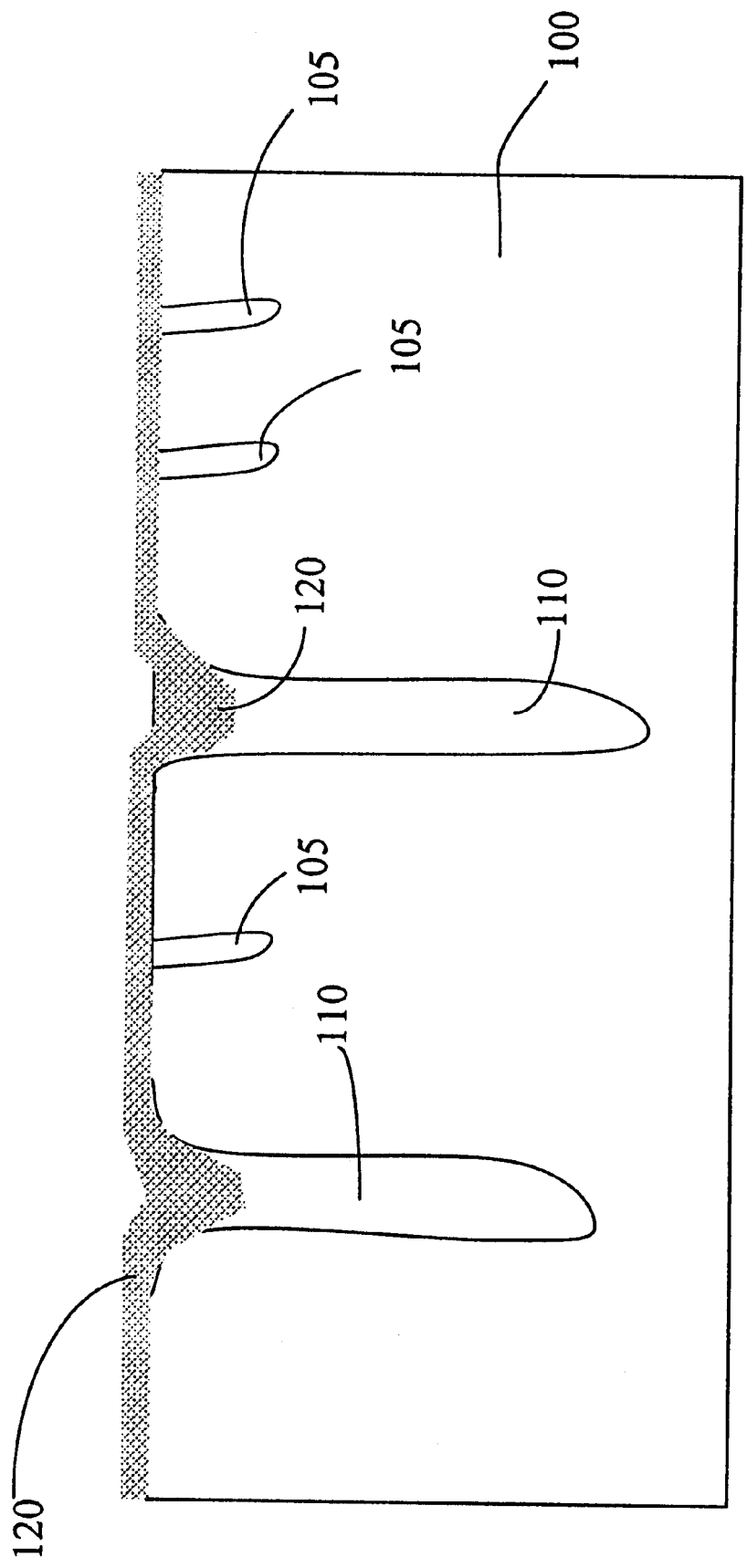
FIG. 1 is a simplified pictorial illustration of apparatus for treating skin in order to prevent and cure acne in accordance with a preferred embodiment of the present invention.

In preferred embodiments of the present invention, the hair ducts are forced to open so that excess oil and unwanted deposition can be removed from the hair duct.

To accomplish this, a substance, which can absorb tight or electromagnetic energy, is forced into the ducts. The light or electromagnetic energy impinging on the target is thus converted into heat. The heated substance then expands under the influence of the thermal energy, thus forcing the pores to expand and open and allow cleaning and drainage of unwanted substance within the hair duct.

The expansion process described above, may include any or all of the following:

Volumetric thermal expansion which is proportional to the inserted/absorbing substance temperature, vaporization, sublimation, rapid vaporization, explosive vaporization, expansion due to plasma formation, expansion due to gas generation, and ablation.

The high absorption substance may also become liquefied at some point following the start of the heating and expansion event, thus enabling drainage and cleaning of the hair duct including the substance of high absorption coefficient or high expansion coefficient itself.

The sequence for the procedure may be as follows:

A) Apply a substance of high absorption to the skin and force said substance down the hair follicle. Wipe off excess substance on surface. Irradiate with pulse duration such that no significant heat is transfer to adjacent tissue and ablative interaction occurs at follicle openings.

B) Applying a substance of high absorption to the skin and force said substance down the hair follicle. Wipe off excess substance on surface. Irradiate with a pulse duration such that no heat is transferred to adjacent tissue and rapid heating and expansion interaction occurs at follicle openings. Pulse duration can be, for example in the range of about one microsecond and as long as about 100 ms, since at these pulse duration ranges thermal diffusion is from about 1 $\mu$m and up to about a few hundred micrometers. Preferred irradiation times are from about 100 microsecond to about 10 millisecond. Such thermal diffusions are acceptable while significant physical expansion of the absorbing substance can be achieved.

C) Alternatively, in another embodiment of the present invention, apply a substance of high absorption to the skin and force said substance down the hair follicle. Wipe off excess substance on surface. Irradiate with pulse duration such that no heat is transferred to adjacent tissue and rapid heating, expansion and melting of "absorbing plug" occurs at follicle openings.

D) Alternatively, in another embodiment of the present invention, apply a substance of high reflection to the surface of the skin. Force that substance down the hair ducts while ensuring that the particles in said substance are such that they are not capable of penetrating (meaning that they are too large) into any other type of skin pores other than the hair follicle (such as surface sweat pores).

In an alternative embodiment of the present invention, a substance of high absorption is applied to the surface and is forced down the hair ducts. The particles in said substance are such that they are not capable of penetrating into any other pores on the skin surface. The surface is then wiped off to allow substantial removal of said substance from the skin surface. The substance of high absorption, however, is substantially not removed from hair duct openings. A source of electromagnetic energy is then allowed to irradiate and subsequently heat and cause expansion to the substance of high absorption at the follicular duct openings. Such an expansion allow drainage and cleaning of the duct openings.

An alternative embodiment contemplates a method and apparatus for both the treatment and prevention of occurrence of acne and is disclosed below.

The method relies on the creation of differential openings in the skin, in particular, differential openings in the human skin.

The phenomena of acne occurs due to improper drainage of the hair follicle opening. The hair follicle opening is approximately on the order of from about 50 $\mu$m to about 100 $\mu$m. The opening of any other pore on the skin is substantially smaller than that. In particular the opening of the sweat pores are less than about 30 $\mu$m in diameter.

The method and apparatus disclosed consists of the following steps:

a) In the event that hair is growing out of the targeted skin area, the first step is to remove the hair shaft of the follicle area. Such removal can be accomplished, for example, by means of wax depilation, mechanical removal or chemically removing the hair from the skin.

b) Applying a substantially reflective coating to skin. The reflective coating comprises a suspension of reflective particles, that are capable of reflecting substantially most of the light impinging on them and absorbing very little of the impinging electromagnetic radiation. For example, metal-based particles could easily reflect over 90% of the incident light.

The reflective particles in the suspension substance should also be of a size that is larger than the size of sweat pores in the skin of the patient. Preferably, the particles in the reflecting substance should be greater than 30 $\mu$m. The particles in the suspension particles, however, should be smaller than the size of the hair follicle opening in the targeted skin area. Preferably, the particles in the reflecting substance should be between about 30 micrometer and about 80 micrometer.

c) Reflecting particles in suspension are rubbed into the skin so that the reflecting coating is covering the skin and sweat pores (or any other openings in the skin). Furthermore, the reflecting particles are forced into the hair follicle openings so that they substantially do not completely block the hair follicle openings.

d) Next, an electromagnetic or other energy source capable of being substantially reflected by the high reflective particles in the suspension is applied to the skin. The applied energy is reflected from most of the skin surface, but is trapped and propagated down the hair follicle to
  i) Remove the substance blocking the opening through the process of ablation, thus allowing enhanced pore drainage.
  Or, alternatively,
  ii) To thermally heat and destroy the blocking substance in the opening of the hair follicle thus allowing enhanced drainage.
  iii) To cause partial or complete destruction of component within the hair follicle and the hair follicle itself, thus allowing enhanced pore drainage or elimination of secretion from the treated follicles.

Since often hair growth is not desired In the areas effected by acne (for example, facial skin) elimination of hair growth might constitute an additional benefit of the hair shaft within the follicle.

e) An alternative embodiment incorporates the use of highly precise interactions such as those generated by very short pulses may be particularly useful since such interactions are limited in space and may minimize any collateral damage in the area adjacent to the targeted opening of the hair follicles. In addition, localization of interaction may be enhanced due to "funneling" of incoming radiation to above-threshold level due to coating of the walls of the follicular openings.

f) In another preferred embodiment, a short pulse of sufficiently high peak power is directed towards a target skin with high absorbing substance confined only to the hair follicles opening (for example, by one of the methods described above). Because of their high peak intensity and the localization of energy density in the high absorbing substance, an explosive interaction will be initiated only in the opening of the hair follicle allowing physical and opening of the hair follicle opening, thus allowing enhanced drainage.

FIG. 1 illustrates the principle of operation of the present invention as described by the embodiment involving a substance of high absorption and high thermal expansion. In this embodiment hair shafts are, if present, first removed from the surface of the skin to be treated for acne. They may be removed by either mechanical, or chemical means or by waxing.

As shown in FIG. 1A, the surface of the skin, 100, is first covered by a substance containing components characterized by a large optical absorption and high thermal expansion 120. These components in the applied substance may or may not be the same material. The substance applied to the skin, 100, may, for example, contain one, two, or more different types of material each serving a different purpose (one may yield significant thermal expansion while the other may yield a significant optical absorption.

The applied substance 120 is then rubbed and forced to penetrate the hair follicle openings 110 on the skin surface. Such a forceful skin penetration may also be accomplished by using an ultrasound or supersonic device to force the material farther into the skin pores. The particles within the applied substance 120 are designed to be large enough where they are unable to penetrate the sweat pores 105, but small enough to allow them to penetrate the hair duct openings 110.

Figure 1B:
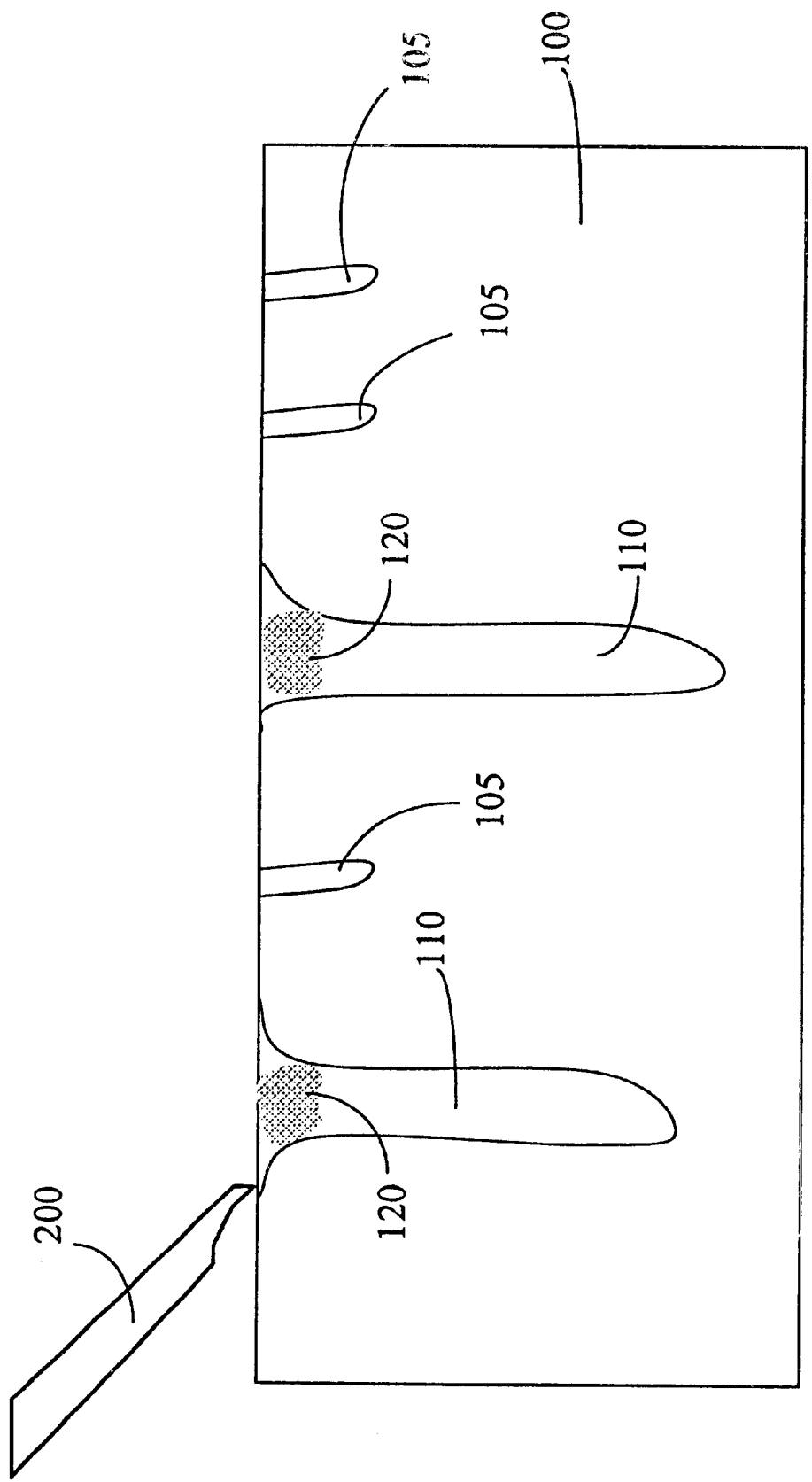

As shown in FIG. 1B, the substance applied to the skin is then scraped off by means of a rigid edge 200 or is simply wiped off the skin surface as shown in FIG. 1B. This results n a relatively clean surface with an accumulation of the substance of high absorption and high expansion 120 substantially only In the hair ducts.

Figure 1C:
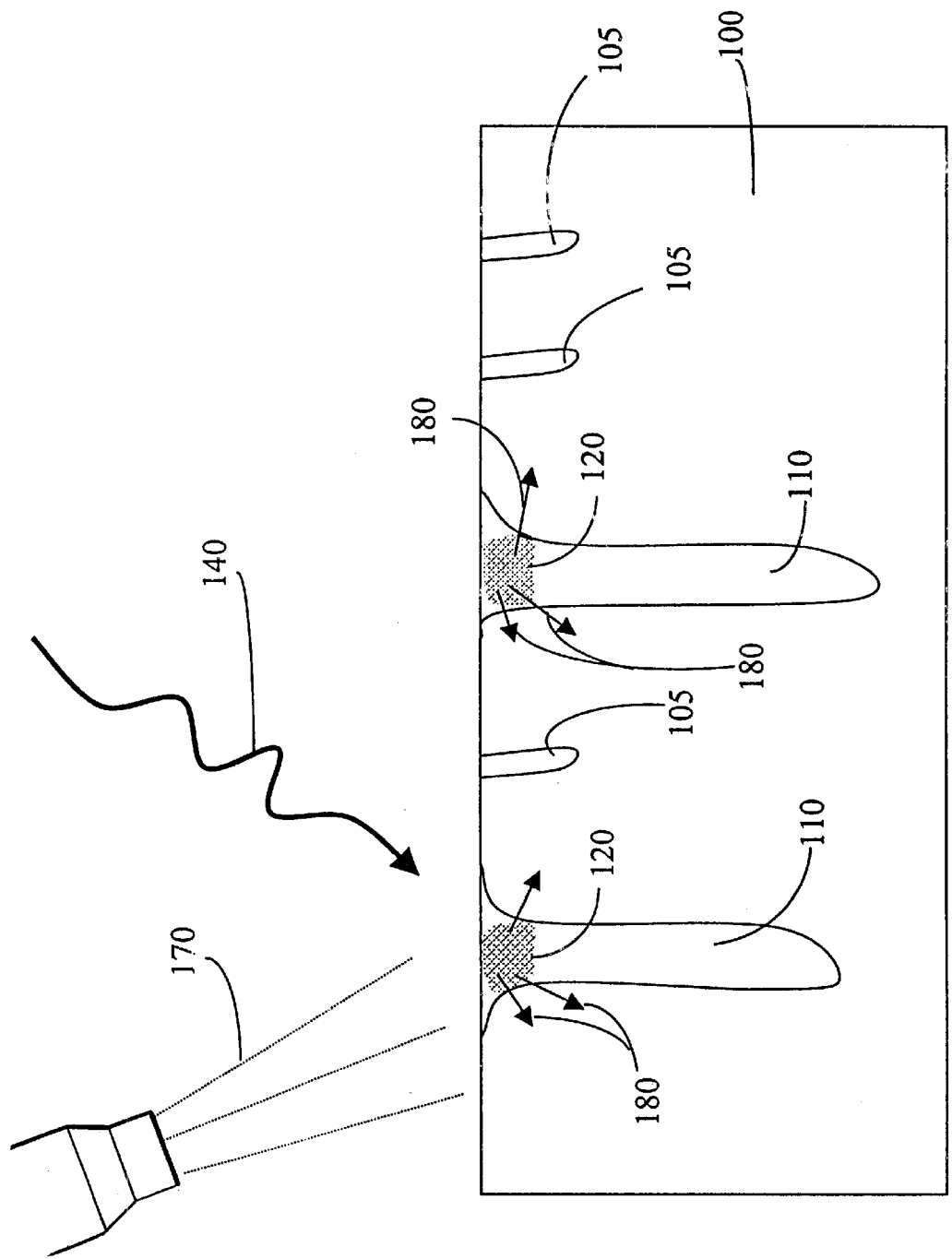

FIG. 1C shows a source of electromagnetic radiation 140 which is substantially not absorbed by the skin but is well absorbed by the substance 120. The resulting radiation 140, is applied to the skin resulting in a rapid expansion of the substance of high absorption and high expansion 120, in the direction shown by the arrows 180. This expansion will allow opening of the pores and drainage of the pores. The heat generated thereof, may also allow localized destruction of bacteria and cleaning and sterilization of infected area. To minimize pain and control the spread of thermal energy a cooling agent 170 (for example, a cryogen spray or a cooled air flow) may also be applied a short time interval after the radiation is applied. Such localized heating and a more global cooling may enhance the expulsion of infected material out of the treated hair follicle ducts. high expansion 120, in he direction shown by the arrows 180. This expansion will allow opening of the pores and drainage of the pores. The heat generated thereof, may also allow localized destruction of bacteria and cleaning and sterilization of infected area. To minimize pain and control the spread of thermal energy a cooling agent 170 (for example, a cryogen spray or a cooled air flow) may also be applied a short time interval after the radiation is applied. Such localized heating and a more global cooling may enhance the expulsion of infected material out of the treated hair follicle ducts.

Additional Embodiments Include:
A) Applying a substance consisting of a suspension of high thermal conductivity (HTC) to the area to be treated. Forcing said substance into the hair ducts. Forcing the HTC substance down the hair ducts, for example, by the use of an ultrasound field. The HTC substance particle should be large enough as to not enter sweat pores or any other opening in the skin other than the hair duct openings (about greater from 40 $\mu$m, but smaller than about 80 $\mu$m). Superficially wiping off the surface of the targeted surface but not removing it from the hair ducts. Applying a heat source or a laser to the surface. The skin is an insulator, so substantially most of the HTC substance will heat up and open up the pores and allow cleaning of the hair ducts.
B) Applying a substance of high absorption to the surface of the skin. Forcing said substance down the hair ducts. The particles in said substance are such that they are not capable of penetrating into any other pores on the skin surface. Wiping the surface off substantially without removing said substance from the hair ducts. Applying electromagnetic radiation to the surface of the skin so that light is substantially absorbed mostly by the substance of high absorption that is retained in the hair ducts. Applying light to selectively ablate or heat only the region of the opening of the hair ducts to allow drainage and cleaning action of the on the hair ducts.
C) Applying a substance of high absorption to the skin and forcing said substance down the hair follicle. Wiping off excess substance of surface. Irradiating with a pulse duration such that no heat is transferred to adjacent tissue and rapid heating and expansion interaction occurs at follicle openings.
D) Applying a substance of high absorption to the skin and forcing said substance down the hair follicle. Wiping off excess substance of surface. Irradiating with a pulse duration such that no heat is transferred to adjacent tissue and rapid heating and expansion interaction occurs at follicle openings.
E) Applying substance of high absorption to the skin and forcing said substance down the hair follicle. Wiping off excess substance of surface. Irradiating with a pulse duration such that no heat is transferred to adjacent tissue and rapid heating, expansion and melting of "absorbing plug" occurs at follicle openings.
F) Applying a substance of high reflection to the surface of the skin. Removing said substance from around the hair ducts. The particles in said reflective substance are such that they are not capable of penetrating (are too large) into any pores on the skin surface.
G) Applying a substance of high absorption to the surface, forcing said substance down the hair ducts. Particles in said substance are such that they are not capable of penetrating into any other pores on the skin surface. Wiping surface off substantially removing said substance from the skin surface but substantially not removing said substance of high absorption from hair duct openings.

I claim:

1. A method for treating acne, the method comprising the steps of:
   applying a reflective coating to a skin area being treated;
   removing the reflective coating proximate a blocked hair follicle; and
   applying electromagnetic energy to the skin area, the electromagnetic energy being substantially reflected by the reflective coating so as to protect tissue and the electromagnetic radiation propagating through tissue where the reflective coating has been removed so as to mitigate blockage of a follicle.

2. The method of claim 1 wherein the area where coating proximate to a blocked hair follicle has been removed is from about 0.1 mm in diameter to about 10 mm in diameter.

* * * * *